United States Patent
Blocher et al.

(10) Patent No.: US 6,520,960 B2
(45) Date of Patent: Feb. 18, 2003

(54) BIPOLAR MEDICAL INSTRUMENT FOR CUTTING TISSUE

(75) Inventors: Martin Blocher, Tuttlingen (DE); Valentino Remorgida, Genua (IT)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/865,273

(22) Filed: May 25, 2001

(65) Prior Publication Data

US 2001/0037108 A1 Nov. 1, 2001

Related U.S. Application Data

(63) Continuation of application No. PCT/EP00/08061, filed on Aug. 18, 2000.

(30) Foreign Application Priority Data

Sep. 28, 1999 (DE) .......................... 199 46 527
Feb. 14, 2000 (DE) ...................... 200 02 645 U

(51) Int. Cl.[7] ............................... A61B 18/18
(52) U.S. Cl. ............................... 606/51; 606/48
(58) Field of Search ..................... 606/41, 42, 45, 606/46, 48–52

(56) References Cited

U.S. PATENT DOCUMENTS 5,290,286 A * 3/1994 Parins ..................... 606/50
5,637,111 A 6/1997 Sutco et al.
5,792,137 A * 8/1998 Carr et al. ................. 606/29
6,030,384 A * 2/2000 Nezhat ..................... 606/48

FOREIGN PATENT DOCUMENTS

WO WO99/05976 2/1999
WO WO99/23960 5/1999

OTHER PUBLICATIONS

Bipolar–Instrument n. Remorgida, 2/98.

* cited by examiner

*Primary Examiner*—Michael Peffley
(74) *Attorney, Agent, or Firm*—St. Onge Steward Johnston & Reens LLC

(57) ABSTRACT

A bipolar medical instrument is provided for cutting tissue. The instrument comprises a first working element and at least one second working element, which are arranged adjacent to one another at a distal end of the instrument. The first working element and the second working element are configured as an electrode connectable to high frequency current and a counter electrode. One of the first working element and the second working element comprises at least one projection, which is directed toward the other working element. The free end of the projection is configured such that a concentration of the current density occurs at the free end.

18 Claims, 6 Drawing Sheets

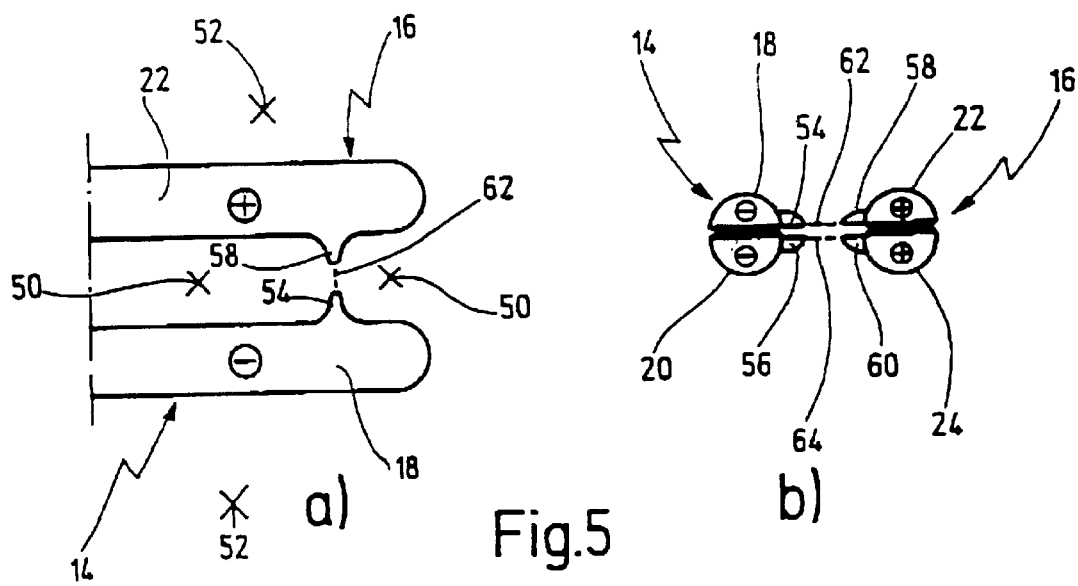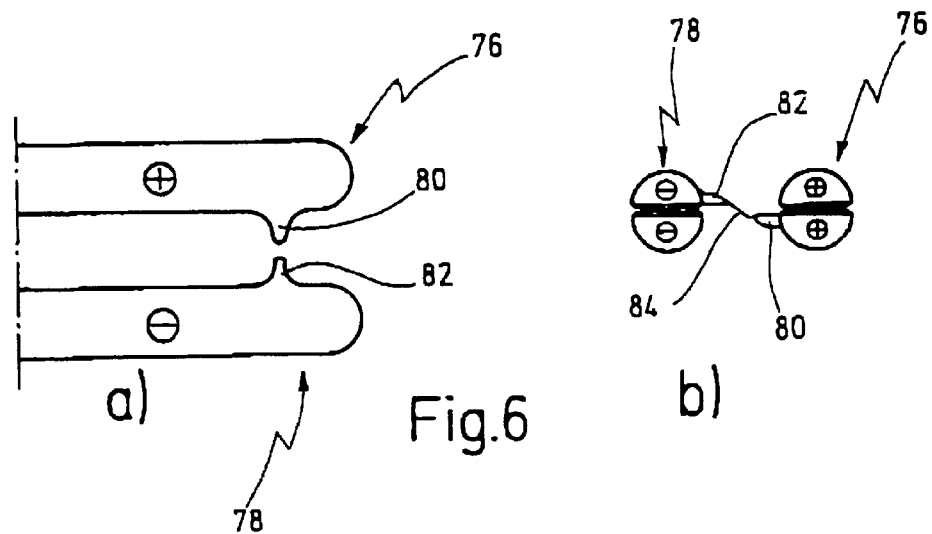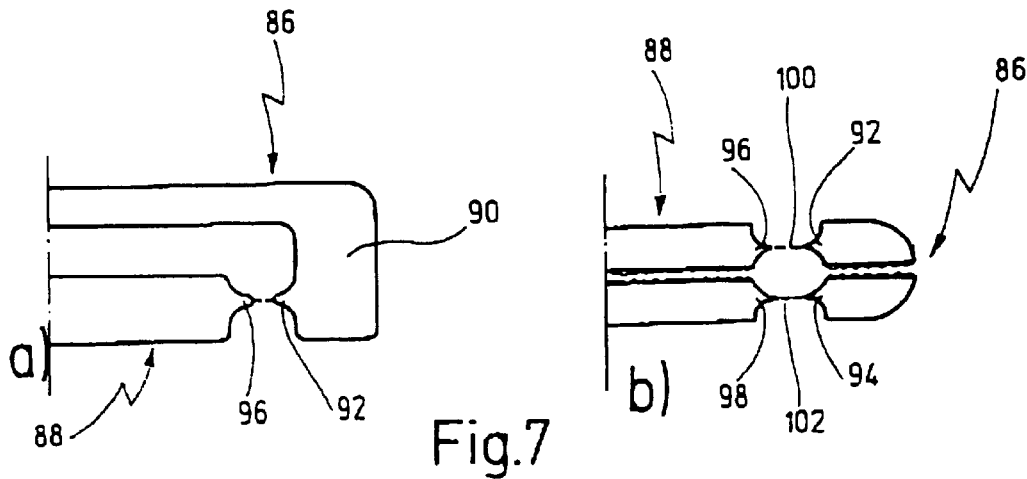

BIPOLAR MEDICAL INSTRUMENT FOR CUTTING TISSUE

CROSS REFERENCE TO PENDING APPLICATIONS

This application is a continuation of pending International application PCT/EP00/08061 filed on Aug. 18, 2000, which designates the United States and claims priority of German patent application DE 199 46 527.4 filed on Sep. 28, 1999 and of German utility model DE 200 02 645.3 filed on Feb. 14, 2000.

BACKGROUND OF THE INVENTION

The invention relates to a bipolar medical instrument for cutting tissue comprising a first working element and at least one second working element, which are arranged adjacent to one another at a distal end of the instrument. The first working element and the second working element are configured as an electrode connectable to high frequency power and a counter electrode.

Such an instrument is disclosed in the German catalogue of the company Karl Storz GmbH & Co. KG, Tuttlingen, "STORZ Karl Storz-Endoskope", Vol. "Laparoskopie", $3^{rd}$ Edition 1/1999, page BI-COA 10/2. Such a bipolar medical instrument is used for example in laparoscopic surgery for treating tissue in the human or animal body.

Incisions are made in the tissue being treated and cause bleeding, which must be stopped.

In the known instrument, bipolar high frequency power is used only for stopping bleeding, i.e. for coagulation. The placement of incisions in the tissue takes place mechanically, namely with a scalpel-like knife.

The known instrument mentioned before comprises a first working element in the form of a jaw and a second working element also in the form of a jaw, where the jaws are arranged side by side at a spacing from one another, in other words like a pair of forceps. The jaw forming the first working element is formed as an electrode which can be supplied with high frequency power and the jaw forming the second working element is formed as a counter electrode. The first jaw can be connected with a corresponding electric line to one pole of a high frequency voltage source and the second jaw can be connected through a corresponding electric line to the other pole of the high frequency voltage source. The first jaw and the second jaw are insulated from one another due to their spacing.

A comparable instrument is disclosed in WO 97/17033. When switching on the high frequency source, a current flux develops in the tissue between the first jaw and the second jaw, so that the coagulation effect is limited to the region between the two sets of jaws. To coagulate a vessel, the vessel is grasped to extend transversely to the jaw.

The cutting function of this known instrument for cutting tissue, in particular for cutting through vessels present in the tissue, is realized with a scalpel-like knife arranged between the first jaw and the second jaw. The knife can be projected forwardly in axial direction by actuating a separate handle at the proximal end of the instrument, for example to cut through a vessel which is grasped to extend transversely to the sets of jaws. The cutting effect of the knife is purely mechanical. By providing the knife between the first and second jaws, the insertion of an additional cutting tool, for example a cutter or a scalpel, into the operation area is avoided as well as the associated exchange of instruments in comparison to other conventional bipolar instruments having only the coagulation function.

Even so, the configuration of this known instrument with the scalpel-like knife for cutting tissue is of disadvantage when the dimensions of the instrument are to be reduced, i.e. when the instrument is to be constructed as small as possible. The known instrument has a diameter of about 10 mm, while a diameter of such instruments of about 5 mm is desirable for some applications.

Reducing the diameter of the known instrument from 10 mm to 5 mm is however not possible for the following reasons. The scalpel-like knife must be placed between the first jaw and the second jaw, so that the first jaw and the second jaw of the known instrument already have a diameter of only 3 mm and are spaced from one another by about 3 mm. A reduction of the total diameter of the arrangement of the first jaw, the second jaw and the scalpel-like knife to 5 mm would require the reduction of the diameter of the first jaw and the second jaw to less than 1 mm. The stability of the jaws, which make up the working elements, is however no longer ensured with such dimensions. A reliable treatment of the tissue with the instrument requires a sufficient stability of the first and second working elements.

A further instrument is disclosed in the mentioned German catalogue on page BI-COA 5/12, which is a grasping and coagulation instrument without a cutting function. Its working element comprises an upper and a lower jaw part. The two jaw parts are configured as a grasping tool and also as an electrode and counter electrode, so that current can flow for coagulation between the jaw parts through the tissue grasped there between.

The present invention however is not limited to improving an instrument that is limited to grasping and coagulation functions. Therefore, the term "working element" will be understood generally in the present invention, as long as the working elements constitute an electrode and a counter electrode independent of their shape or other functions.

Generally, the object of the present invention is to provide a bipolar instrument for cutting tissue of the above- mentioned type, by which the cutting function is realized in a manner, which is not mechanical.

SUMMARY OF THE INVENTION

The object is achieved by a bipolar medical instrument for cutting tissue, comprising:
  a shaft having a distal end and a proximal end;
  a first working element disposed at said distal end of said shaft, said first working element being configured as an electrode connectable to high frequency current;
  at least one second working element disposed at said distal end of said shaft and adjacent to said first working element, said at least one second working element forming a counter electrode with respect to said first working element,
    wherein at least one of said first working element and said second working element comprises at least one projection, which is directed toward the other of said first and second working elements, and a free end of said at least one projection is configured such that a concentration of the current density occurs at said free end.

The advantageous effect of concentrating the current density in the present instrument is that an incision can be made in the tissue or a vessel in the tissue can be cut off using electrical energy. Compared to the known instrument, the function of cutting is therefore not realized with a mechanical cutting instrument, such as a scalpel-like knife, but with an "electric blade". The placement of an incision with the present instrument is guided by hand such that the "electric cutter" formed between the at least one projection and the other working element is moved through the tissue or through the vessel. The cutting process itself takes place substantially without contact.

Although the invention is not limited to improving the mentioned conventional instrument, also the use of the present invention with this known instrument has the particular advantage that the jaw forming the first working element and the jaw forming the second working element can be formed with larger diameter and therefore are more stable due to the lack of a mechanical cutting instrument between the two sets of jaws in the known instrument. This is the case, even when the total diameter of the instrument should be reduced, for example to 5 mm. In this case, the further advantage results with the present configuration of the invention, that no further handle need be provided on the instrument for cutting the tissue, as is the case in the known instrument, where the scalpel-like knife is moved back and forth. In contrast, the cutting procedure in the present instrument takes place with the working elements themselves, so that the constructive complexity of the present instrument is advantageously reduced.

In a preferred embodiment, both the first working element and the second working element comprise at least one projection.

The feature advantageously leads to increased concentration of the current density between the first and second working elements, where the electric cutting effect can be further improved.

Preferably, the at least one projection of the first working element stands opposed to the at least one projection of the second working element.

The advantage is that the cutting line, defined by the opposing projections, is very precisely defined. The projections can be oppositely disposed in axial direction of the working elements or in a transverse or perpendicular direction. For example, cutting can be performed when the projections are disposed oppositely in perpendicular direction by an axial shifting of the instrument or by a transverse movement with respect to the axial direction of the working elements. When the projections are disposed oppositely in axial direction, cutting can be performed by rotating the instrument about its longitudinal axis.

Preferably, the first working element extends beyond the second working element in axial direction of the working elements and the projections are oppositely disposed in the axial direction of the working elements.

In a further preferred embodiment, the free end of the at least one projection is configured as a point.

With this configuration of the free end as a point, particularly high current densities and therefore a particularly good cutting effect can be achieved du e to the effect of the pointed free end. In addition, the "electric blade" defined by the at least one projection can be particularly precisely defined.

The free end of the at least one projection can however also be formed as an edge running transversely to the working element direction to be able to better cut through the entire thickness of the tissue located between the first working element and the second working element. This can also be achieved in that a projection is arranged on each of the two working elements at about the same axial position, whose free ends are also formed as points as described above.

In a further preferred embodiment, the at least one projection can also be rounded.

In this embodiment, a high current density is not achieved as with the pointed projection, however the electric cutting effect can advantageously be expanded to a strip corresponding to the width of the rounded free ends.

A particularly sharp and well—defined short incision can be made advantageously when the free end of the at least one projection of the first working element and the free end of the at least one projection of the second working element have a minimal spacing with respect to one another, because the current flow is then optimally concentrated with high density in the short path between the projections. "Minimal" spacing means that the spacing of the working elements in the region of the projections is smaller than that in the remaining regions of the working elements. For example, a minimal spacing can be about 1 mm or less.

The free end of the at least one projection can preferably be configured as an elongated edge.

Further preferred is when at least one projection runs as a wedge with an inclination in the axial direction of the working element. It is also preferred to provide both the first working element and the second working element with at least one projection formed as an elongated edge, where the edges are each sloped with respect to the axial direction of the working elements and where the slopes of the opposing edges run counter directionally.

As can be taken from above, an electric cutting of the tissue along a defined cutting line is made possible by a corresponding selection of the arrangement of the at least one projection, preferably several projections. In the scope of the present invention, it is therefore possible to generate one or more defined cutting lines for electric cutting by correspondingly selecting the number and position of one or more projections.

A particularly advantageous adaptation of the present instrument to the given application is made possible in that the first working element and the second working element are both exchangeable. Thus, different working elements with a corresponding number and distribution of the projections can be made available.

In a constructively particularly simple embodiment of the present invention, the first working element and the second working element are preferably arranged to be immovable on the distal end of one or two rod-shaped elements.

In this manner, a purely bipolar cutting instrument is advantageously provided, which can be used as a type of scalpel or knife for cutting tissue or for cutting through vessels. The difference however is that the cutting effect is produced electrically instead of mechanically. Preferably, the rod-shaped element or the rod- shaped elements are configured themselves to conduct electricity.

A constructively simple arrangement of the present instrument is achieved thereby, because no separate wires are necessary for supplying electricity. The at least one rod-shaped element or the rod-shaped elements can be equipped with a simple handle for manipulation at the proximal end.

It is however also preferred that the first working element and the second working element are each formed as jaws, where the first set of jaws and the second set of jaws are arranged side by side at a spacing from one another, and where each set of jaws comprises two jaw parts moveable relative to one another between which the tissue can be grasped and coagulated.

This advantageous embodiment represents an improvement of the above-mentioned known grasping, coagulating and cutting instrument, where according to the invention, the scalpel-like knife provided between the first and second sets of jaws in the known instrument is now replaced according to the present invention by the at least one projection and the electric cutting effect produced therewith. With this instrument, tissue can first be grasped and coagulated between the jaw parts. To subsequently apply an incision or to cut through a vessel, the jaw parts are opened and the instrument is withdrawn by a small amount. The jaw parts are closed and the instrument is then guided such that the "electric blade" formed between the at least one projection of one jaw and the other jaw passes through the tissue and cuts same.

In a further preferred embodiment, the at least one projection is arranged on the first jaw part of one jaw and a second projection is arranged on the second jaw part of the same jaw.

The advantage is that an "electric blade", is formed having a spatial and not only linear extension between the two working elements of the instrument when the jaw parts are closed or even more so when the jaw parts are slightly opened. Particularly advantageous is when the other jaw also comprises at least two projections, of which one projection is on the first jaw part and the second projection is on the second jaw part of the other jaw.

In a further preferred embodiment, the at least one projection of the first jaw is arranged on one first jaw part and the at least one projection of the second jaw is arranged on the jaw part of the second jaw which lies diametrically opposite to the first jaw part of the first jaw.

In this embodiment, a cutting line is achieved which runs at an inclination with respect to the main plane (horizontal plane) defined by the first and second jaws.

Preferably, the at least two projections in the above two embodiments are arranged at the same location along the axial direction of the working elements.

The advantage of this arrangement is that a precise incision can be made from both sides in a given piece of tissue.

Further advantages of the invention will become apparent from the following description and the appended drawings. It will be understood that the above-mentioned features and those to be discussed belong are applicable not only in the given combinations, but may also be used in other combinations or taken alone without departing from the scope of the present invention.

Embodiments of the present invention are illustrated in the drawings and will be described in detail below.

BRIEF DESCRIPTION OF THE DRAWINGS

FIGS. 5a) and b) show a schematic plan view (FIG. 5a) and a front view (FIG. 5 b) of the first and second working elements of FIG. 2;

FIGS. 6 a) and 6b) show a schematic plan view (FIG. 6a) and a front view (FIG. 6b) of the first and second working elements of FIG. 4;

FIGS. 7a) and 7b) show a schematic plan view (FIG. 7a) and a side view (FIG. 7b) of a further embodiment of the first and second working elements for use in the instrument of FIG. 1;

DETAILED DESCRIPTION OF PREFERRED EMBODIMENTS

Figure 1:
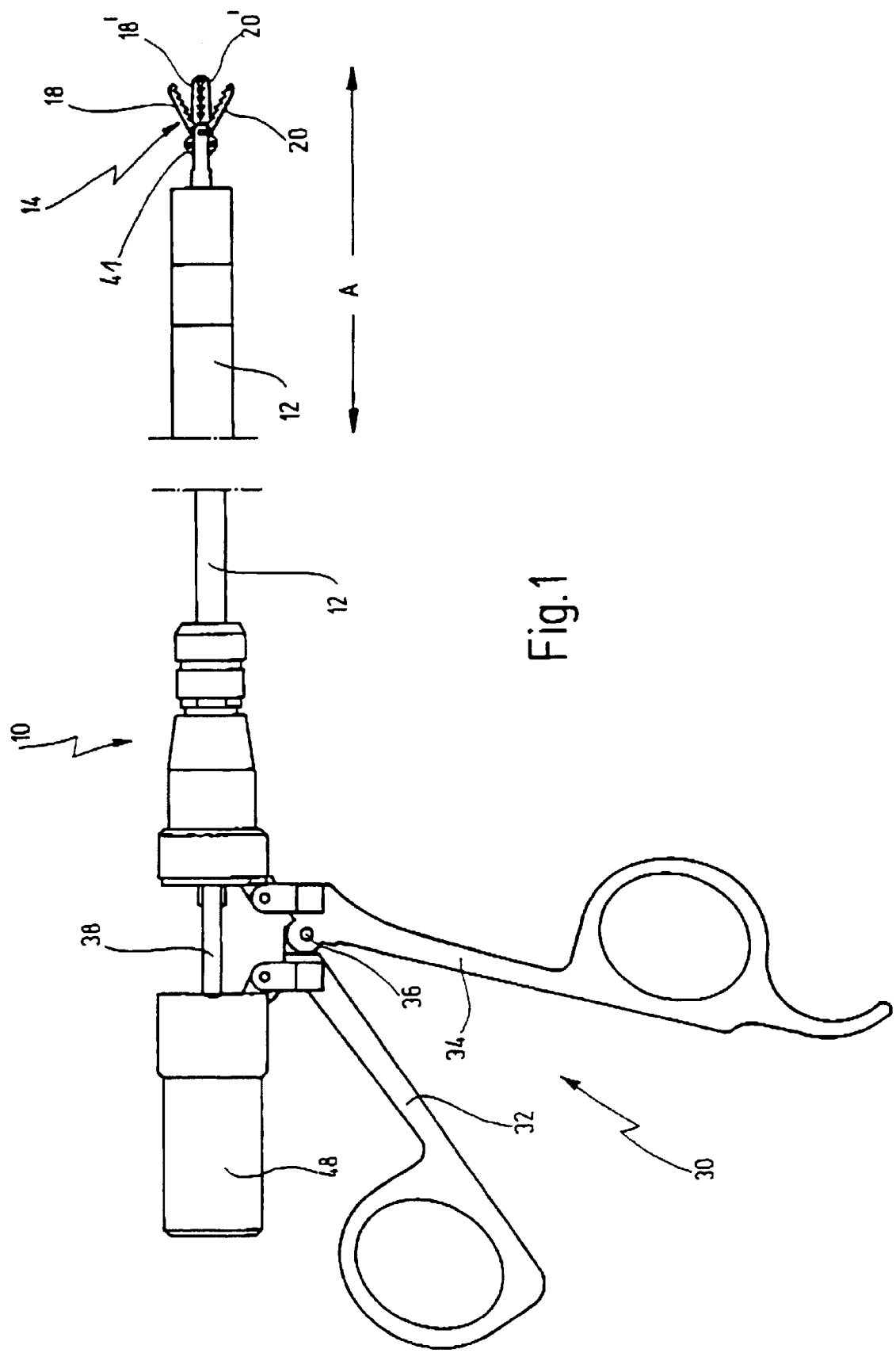
FIG. 1 shows a side view in two parts of a bipolar medical instrument for cutting tissue, where the distal portion of the instrument is illustrated with enlarged scale.

FIG. 1 shows a bipolar medical instrument for cutting tissue generally indicated with the numeral 10. The instrument 10 not only allows the cutting of tissue, but also the grasping and coagulation of tissue, as will be described in detail below. The instrument 10 is used in minimally invasive surgery for treating tissue.

The instrument 10 comprises an elongated shaft 12, where the distal portion indicated with A in FIG. 1 is shown with enlarged scale.

Figure 2:
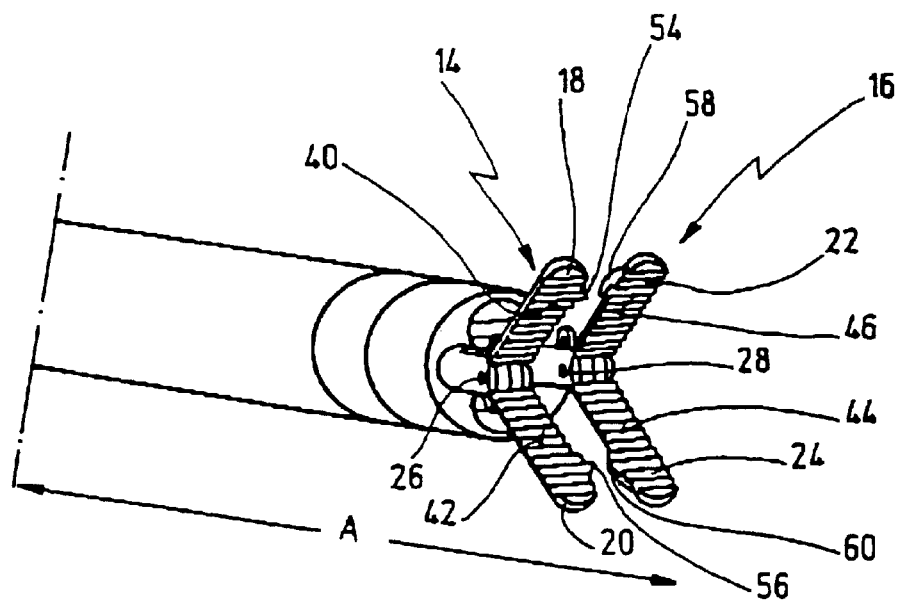
FIG. 2 shows a perspective illustration of the distal portion of the instrument in FIG. 1 with a further enlarged scale.

The portion A is shown in perspective in FIG. 2 with greater enlargement.

The shaft 12 is formed as a tubular shaft. A first working 14 and an adjacent second working element 16 are arranged at the distal end of the shaft 12, where only the right first working element 14 can be seen in the side view of FIG. 1. The working elements 14 and 16 are each formed as jaws.

The first working element 14 comprises a first jaw part 18 and a second jaw part 20.

The second working element 16 comprises a corresponding first jaw part 22 and a second jaw part 24.

The first jaw part 18 and the second jaw part 20 are moveable relative to one another. In the embodiment of FIG. 2, both the first jaw part 18 and the second jaw part 20 are moveable, namely they are both pivoted on a pivot axis 26. Similarly, the first jaw part 22 and the second jaw part 24 of the second working element 16 are moveable relative to one another, namely the two jaw parts 22, 24 are pivoted on a pivot axis 28.

In FIG. 1, the working element 14 is illustrated with its jaw parts 18, 20 in the open position and with the numerals 18' and 20' in its closed position.

As can be taken from FIG. 2, the first working element 14 and the second working element 16 are arranged adjacently to be side by side at a spacing from one another. In particular, the first working element 14 and the second working element 16 are arranged parallel to one another and can be opened and closed in synchronization.

To open and close the first working element 14 and the second working element 16, the instrument 10 comprises a handle 30 including two grips 32, 34, which are moveable relative to one another. The grip 32 and the grip 34 are pivotally connected to one another through a pivot axis 36.

The grip 32 is connected to the first working element 14 or the second working element 16 in force-locking manner through a force transmission mechanism including two push and pull rods, of which only the right rod 38 can be seen in FIG. 1. The push and pull rod 38 as well as the rod running parallel thereto and not visible in FIG. 1 are connected through a toggle lever arrangement 41 with the corresponding working elements 14 and 16.

The jaw making up the first working element 14 and the jaw making up the second working element 16 are synchronously closed when pressing the first and second grips 32, 34 together. By moving the grips 32, 34 apart from one another, the first and second jaws are synchronously opened.

According to a first function of the first and second working elements 14, 16, the jaw parts 18, 20 and 22, 24 are configured as grasping tools, i.e. the inner sides 40, 42, 44, 46 of the corresponding jaw parts 18, 20, 22, 24 are formed as a surface and additionally provided with ridges to improve the griping capabilities of the inner sides for grasping and securely retaining tissue.

According to a further function of the first and second working elements 14, 16, the first working element 14 is configured as an electrode connectable to high frequency power a and the second working element 16 is configured as a counter electrode to coagulate tissue held between the jaw parts 18, 20 and 22, 24. The jaw parts 18, 20 and 22, 24 are configured to be electrically conductive at least on their inner sides 40 to 46 or are completely made of metal.

The first working element 14 is connected to a first contact pole (not shown) of a socket connector 48 at the proximal end of the instrument 10 in FIG. 1 through a conductor formed by the associated push and pull rod. The second working element 16 is connected to the other contact pole of the socket connector 48 through the other push and pull rod as a conductor. A high frequency power cable (not shown) can be connected to a socket connector 48, which is connected to or can be connected to an external high frequency voltage source (not shown).

FIG. 5 gives a schematic illustration of the first working element 14 and the second working element 16 alone, where the sign + indicates that the second working element 16 forms one electrode and the sign − indicates that the first working element 14 forms the counter electrode. Thus, the working elements 14 and 16 have different electrical potentials.

No insulation is necessary between the first and second working elements 14, 16 because the first working element 14 and the second working element 16 are spaced from one another, where the arrangement of the two working elements 14, 16 being side by side at a spacing which has proven itself for small bipolar instruments.

When supplying electricity to the first working element 14 and the second working element 16, the tissue grasped between the inner sides 40, 42 and 44, 46 are coagulated by the high frequency current. The coagulation effect is limited to the intermediate space 50 between the first and second working elements 14, 16, so that tissue outside of this region is not affected by the high frequency current. No current flows and correspondingly no coagulation occur in regions outside of the first and second working elements 14, 16, as indicated with 52.

The instrument 10 also has a third function, namely that tissue and also vessels in the tissue, which are held by the first and second working elements 14, 16, can be cut and separated electrically through the effect of the high frequency current.

For this purpose, at least one of -the working elements 14 or 16, in the embodiment of FIG. 2 both the first and second working elements, comprises at least one projection, in the embodiment of FIG. 2, two projections. The jaw part 18 of the working element 14 and the jaw part 22 of the working element 16 each comprise an opposing projection and the jaw part 20 of the working element 14 and the jaw part 24 of the working element 16 comprise opposing projections. The projection of the jaw part 18 and the projection of the jaw part 20 of the same working element 14 are located at the same position in axial direction of the working element. Similarly, the projections of the jaw parts 22 and 24 of the second working element are also located at the same position along the axial direction of the working element.

A first projection 54 is arranged on the first jaw part 18 and a second projection 56 on the second jaw part 20 of the first working element 14. A first projection 58 is arranged on the first jaw part 22 and a second projection 60 on the second jaw part 24 of the second working element 16.

The projections 54 and 56 of the first working element 14 are directed toward the second working element 16. Conversely, the projections 58 and 60 are directed toward the first working element 14.

Each free end of the projections 54 to 60 is configured such that a concentration of the current density of the high frequency current arises. This is achieved by the shape of the projections 54 to 60, more precisely t he shape of the free ends of these projections 54 to 60, having a point so that the electric field strength reaches a maximum at the points compared to the remaining regions of the first and second working elements 14, 16.

The projections 54 to 60 are positioned such that the projections 54 and 58 and the projections 56 and 60 oppose one another directly with a minimal spacing.

The field lines with maximal concentration of the current density are indicated in FIG. 5 with the dashed lines. With the first and second working elements 14, 16, tissue and vessels therein can be cut along the field lines by the high frequency current due to the maximal concentration of the current density. To cut a vessel, the instrument 10 is held such that the field lines run transversely to the axis of the vessel.

In the embodiment of FIG. 5, the projections 54 to 60 run transversely to the axial direction of the jaws of the first working element 14 and the second working element 16, where the instrument 10 is held for cutting a vessel such that the vessel is located between the working elements 14, 16 and extends parallel to these elements.

In addition, all four projections 54 to 60 are arranged at the same location in the axial direction of the jaws. The positioning of the projections 54, 56 or 58, 60 allows the tissue to be cut from both sides, namely along the defined cutting lines 62, 64.

It will be understood that the projections 54 to 60 are formed of a metal and are connected to be electrically conductive with the respective jaw parts 18 to 24. The projections 54 to 60 can be produced by removing material in a shaping process to manufacture the jaw parts 18 to 24, when the jaw parts 18 to 24 are fabricated from a solid piece of material.

Tissue is treated as follows with the instrument 10 and the working elements 14 and 16 shown in FIGS. 5 a) and 5 b).

The tissue to be treated is first placed between jaw parts 18, 20 and 22 and 24 when the jaw parts are open, whereafter the jaw parts 18, 20 and 22, 24 are closed.

When switching on the high frequency voltage source, bipolar high frequency current flows between the first and second working elements 14, 16 and the tissue held between the jaw parts 18, 20 and 22, 24 is coagulated. If a vessel in the tissue is to be coagulated, the tissue is grasped such that the vessel extends transversely to the working elements 14, 16.

The jaw parts 18, 20, and 22, 24 are opened again in order to subsequently cut the tissue or separate a vessel therein. The instrument 10 is slightly retracted to release from the tissue and the jaw parts 18, 20 and 22, 24 are then closed.

The instrument 10 is then rotated by about 90° about its axis, where after cutting can take place with the closed jaw parts 18, 20 and 22, 24 along the cutting lines 62, 64 formed between the projections 54, 58 and 56, 60 by advancing the instrument 10.

As can be taken from the above description, the instrument 10 unifies the three functions of grasping, coagulating and cutting of tissue due to the configuration of the first working element 14 and the second working element 16.

The projections 54, 58, and 56, 60 are spaced from one another at their free ends by a minimal distance, approximately 1 mm.

An "electric blade" is formed between the first and second working elements 14, 16 by the provision of a projection 54 and 56 respectively on the first jaw part 18 and the second jaw part 20, similarly on the jaw parts 22, 24 of the second working element 16. The "blade" has a height corresponding approximately to the distance between the projections 54 and 56 on the one hand and the projections 58 and 60 on the other hand.

Figure 3:
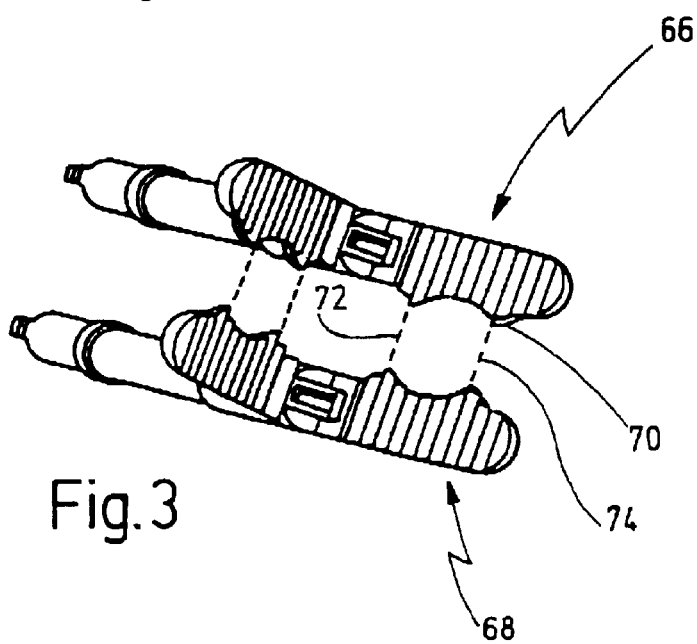
FIG. 3 shows a perspective view in greatly enlarged sc ale of a further embodiment of a first and second working element of the instrument in FIG. 1.

FIG. 3 illustrates a modified embodiment compared to FIG. 2 of a first working element 66 and a second working element 68, which are both formed as jaws as are the working elements 14, 16. Both the first working element 66 and the second working element 68 each comprise four projections 70, i.e. a total of eight projections 70. In this embodiment, two spaced cutting lines 72, 74 result in axial direction of the working elements.

A further difference between the first and second working elements 66, 68 of FIG. 3 and the first and second working elements 14, 16 of FIG. 2 is that the first and second working elements 66, 68 have one moveable jaw part and one immovable jaw part. The respective jaw parts however are moveable relative to one another as in the embodiments of FIGS. 1 and 2.

Figure 4:
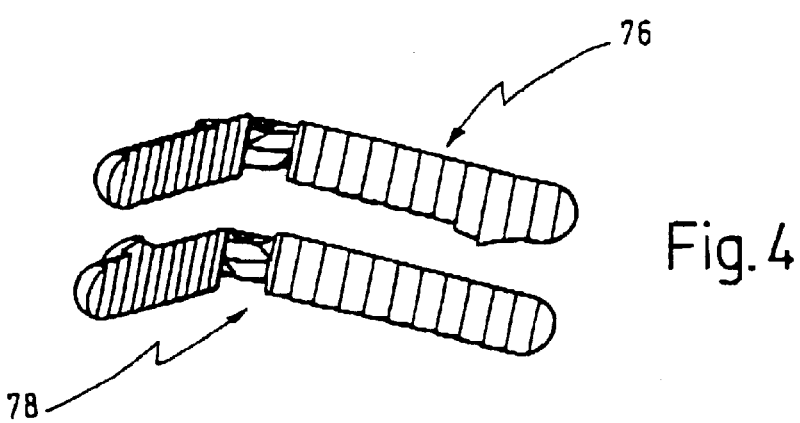
FIG. 4 shows a perspective view in greatly enlarged scale of a further embodiment of a first and second working element for the instrument in FIG. 1.

FIGS. 4 and 6 illustrate a further embodiment of the first and second working elements 76, 78. In this embodiment, the first working element 76 and the second working element 78 each comprise only one projection 80, 82, where the projection 80 and the projection 82 are arranged on a jaw part of the first working element 76 and the second working element 78, such that they are diametrically opposed to one another. In this manner, a cutting line 84 is produced which runs at an angle with respect to the main plane of the first and second working elements 76, 78, i.e. is inclined with respect to the horizontal.

A further embodiment of the first and second working elements 86, 88 as shown in FIG. 7, which differs from the previous embodiment in that the first working element 86 extends beyond the second working element 88 in axial direction of the working elements. The first working element 86 and the second working element 88 are again arranged side by side and spaced from one another. However, first jaw 86 is L-shaped, where a section 90 running transversely to the axial direction of the working elements is arranged in front of the outer distal end of the working element 88.

The first and second working elements 86, 88 each comprise two projections 92, 94 and 96, 98, which in contrast to the above embodiments run along the axial direction of the working elements. The cutting lines 100, 102 are also directed along the axial direction. With this arrangement of the projections 92 to 98, a vessel extending transversely to the axial direction of the working elements can be cut with the first and second working elements 86, 88 by rotating the instrument about its axis or by moving the working elements in the direction transversely to the axial direction.

Figure 8:
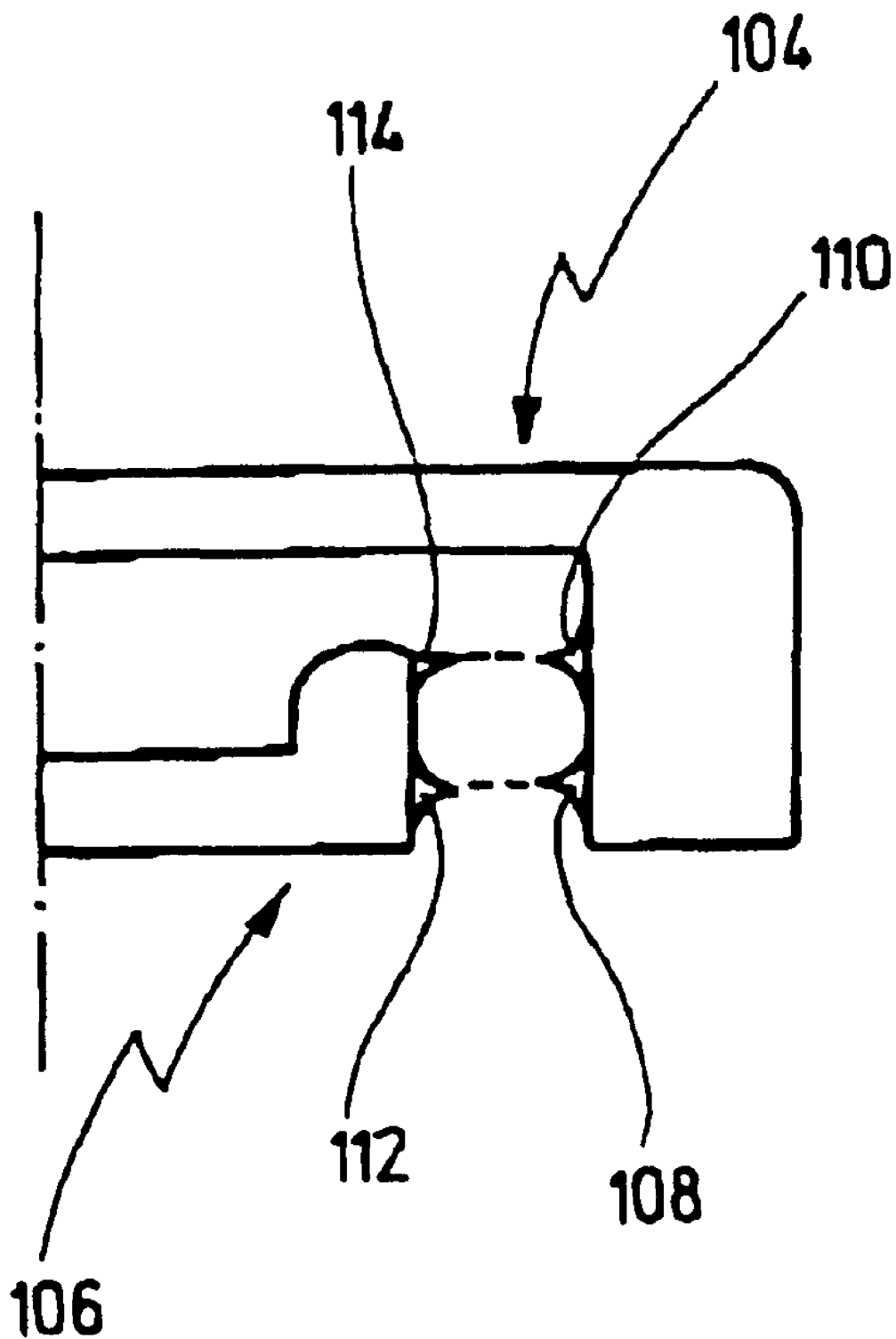
FIG. 8 shows a plan view of a modified embodiment of the first and second working elements compared to FIG. 7.

FIG. 8 shows a modified embodiment compared to FIG. 7, by which each jaw part of the first working element 104 and each jaw part of the second working element 106 comprises two adjacent projections 108, 110 and 112, 114.

All of the above embodiments can be used in the instrument 10 shown in FIG. 1. The instrument 10 is configured such that the first working element 14 and the second working element 16 are removable, such that the jaws 66, 68; 76, 78; 86, 88 or 104, 106 illustrated in FIGS. 3 to 8 can be mounted instead of the first working element 14 and the second working element 16.

Figure 9:
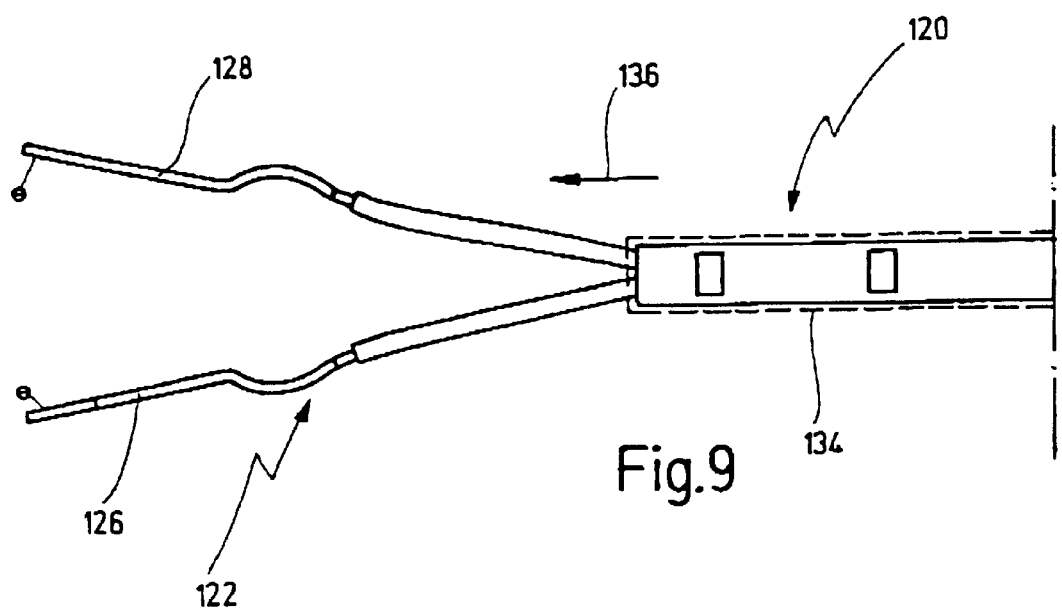
FIG. 9 shows a side view of a further embodiment of a bipolar instrument for cutting tissue in the region of its distal end.
Figure 10:
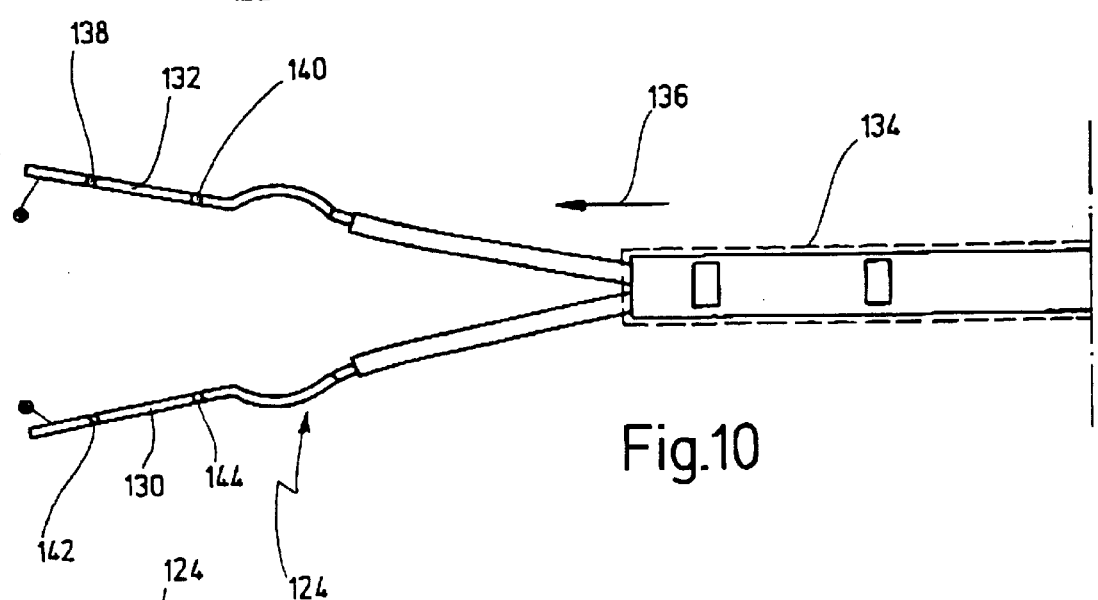
FIG. 10 shows the instrument of FIG. 9, where one of the working elements has been left out.
Figure 11:
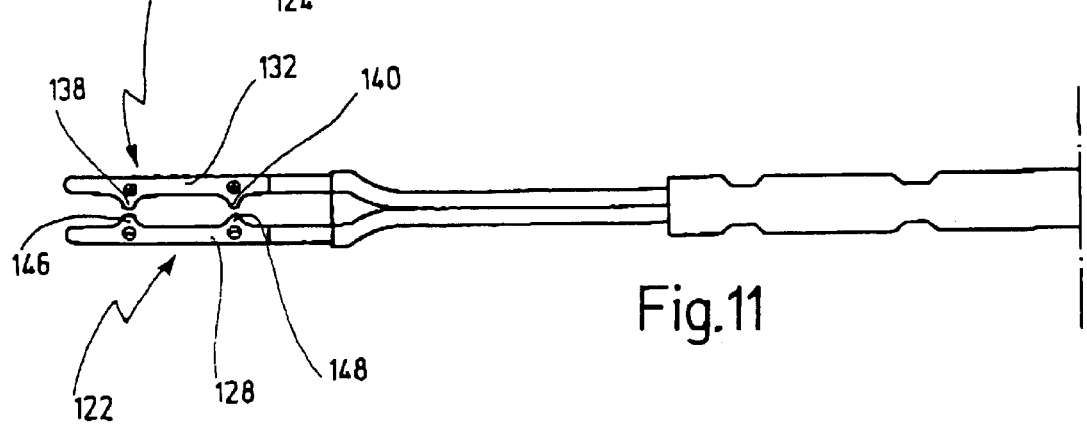
FIG. 11 shows a plan view of the distal end of the instrument of FIGS. 9 and 10.

A further embodiment of a bipolar instrument for cutting tissue is shown in FIGS. 9 to 11, where the instrument 120 unifies the functions of grasping, coagulating and cutting as in instrument 10.

Instrument 120 comprises a first working element 122 and a second working element 124, which are both configured as jaws. The outside of the first working element 122 (left working element) can be seen in FIG. 9, while the inside of the second working element 124 (right working element) can be seen in FIG. 10.

The first working element 122 comprises a first jaw part 126 and a second jaw part 128. Similarly, the second working element 124 comprises a first jaw part 130 and a second jaw part 132.

The jaw part 126 and the jaw part 128 of the first working element 122 are moveable relative to one another, i.e. can be moved out of the open position shown in FIG. 9 into a closed position. The same holds for the jaw parts 130, 132 of the second working elements 124.

The difference between the first and second working elements 122, 124 and the first and second working elements 14, 16 of the instrument 10 is that the jaw parts 18, 20 and 22, 24 of the instrument 10 are connected to one another through a pivot joint, while the jaw parts 126, 128 and 130, 132 are formed as resiliently spreading elements, which can be pushed together by a relative movement of a slide tube 134 indicated with broken lines in FIGS. 9 and 10. When moving the slide tube 134 relative to the jaw parts 126, 128 and 130, 132 in the direction of the arrow 136, the jaw parts 126 to 132 are closed. They open automatically again under reverse motion of the slide tube 134 relative to the jaw parts 126 to 132. This opening and closing mechanism is already known from the German utility model DE 298 23 913, to which reference is made concerning the details of the mechanism.

Similar to the embodiment of FIG. 3, the jaw parts 126 to 132 on their opposing sides each comprise two projections 138, 140 (jaw part 132), 142, 144 (jaw part 130), 146, 148 (jaw part 128) as well as two corresponding projections on the jaw part 126 which are not visible in the figures. The working elements 122, 124 form an electrode and a counter electrode, which is indicated with − and +.

Concerning the cutting function of the instrument 120, the configuration of the working elements 122, 124 correspond to the working elements 66, 68 in FIG. 3, so that reference is made to the description there.

Figure 12:
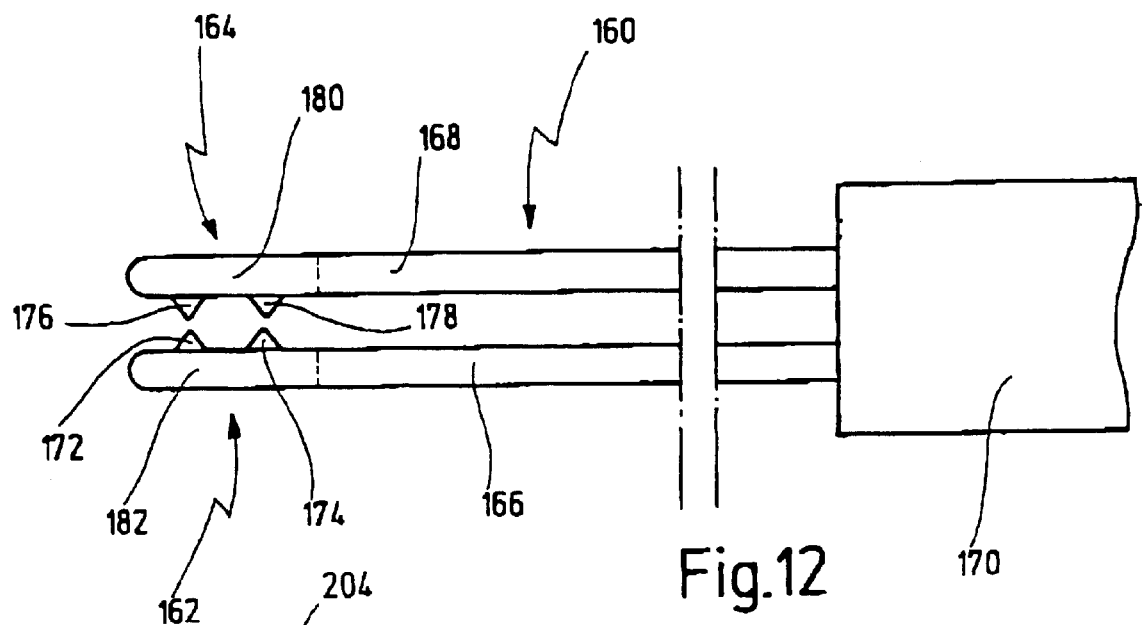
FIG. 12 shows a plan view in schematic illustration of a further embodiment of a bipolar instrument for cutting tissue.
Figure 13:
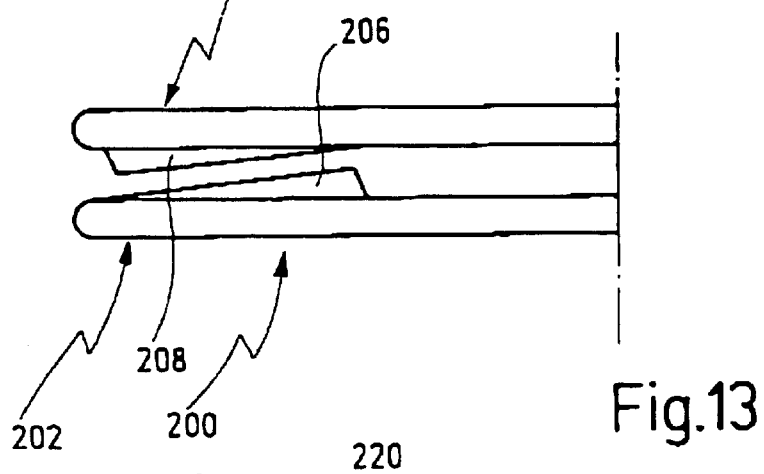
FIG. 13 shows an embodiment modified in comparison to FIG. 12 of a further instrument for cutting tissue, where the instrument is shown only in the region of its working elements.
Figure 14:
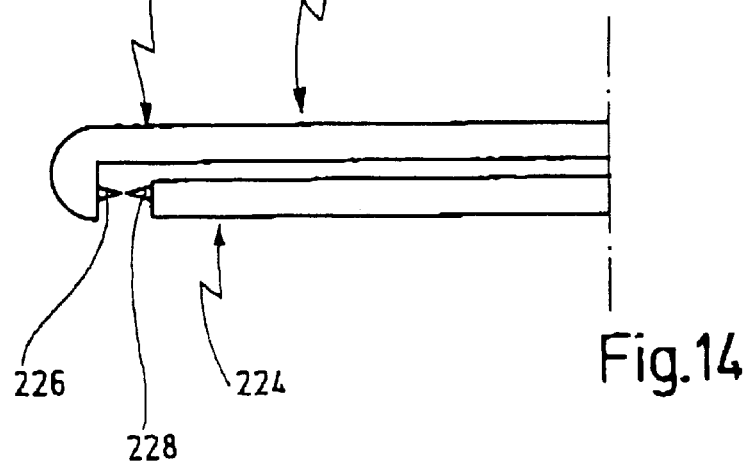
FIG. 14 shows a further embodiment of an instrument for cutting tissue, where the instrument is shown only in the region of its working elements.

Further embodiments of bipolar instruments for cutting tissue are shown in FIGS. 12 to 14. These instruments differ from the above instruments in that the first and second working elements are not formed as jaws, but the working elements are formed to be immovable. Thus these instruments have a pure cutting function, optionally a coagulating function, however no grasping function.

FIG. 12 gives a schematic illustration of a bipolar instrument 160 for cutting tissue.

The instrument 160 comprises a first working element 162 and second working element 164, where the first and second working elements 162, 164 are again arranged to be adjacent to one another.

The working element 162 and the working element 164 are not configured as jaws as above, but as immovable elements arranged at the distal ends of respective rod-shaped elements 166, 168 with which the immovable elements are formed in integral construction.

The rod-shaped elements 166, 168 also simultaneously supply electric power from a proximal high frequency electric connection (not shown), which preferably is arranged at a proximal end of a handle 170.

The first working element 162 correspondingly forms an electrode and the second working element 164 a counter electrode of the instrument 160.

The first working element 162 comprises two projections 172, 174 on the side facing the second working element 164, while the second working element 164 comprises two projections 176, 178 opposing the projections 172, 174.

The rod-shaped elements 166, 168 as well as the working elements 162, 164 can be provided with an electric insulation completely about their circumference, so that only the projections 172 to 178 expose bare metal. However, the working elements 162, 164 can also be left as bare metal in the regions indicated with the numerals 180, 182, so that only the rod-shaped elements 166, 168 have an insulating mantle.

The instrument 160 provides an "electric knife" with which tissue can be cut and vessels can be cut through. When the regions 180, 182 of the working elements 162, 164 have at least partially exposed bare metal, the instrument 116 can also be used for coagulating at the surface regions of the working elements 162, 164.

FIG. 13 shows a slightly modified embodiment compared with FIG. 12 of an instrument 200, whose working elements 202, 204 each comprise a projection 206, 208 configured as elongated edges.

The elongated edges 206, 208 run at an inclination with respect to the axial direction of the working elements as can be seen in FIG. 13. The orientation of the edge of the projection 206 is counter-directional with respect to the orientation of the edge of the projection 208, which can be also taken from FIG. 13.

The instrument 200 shown in FIG. 13 also serves as a knife with an electric cutting function.

Finally, a bipolar instrument 220 for cutting tissue is shown in FIG. 14, which comprises a first working element 222 and a second working element 224. The first working element 222 extends axially beyond the second working element 224, analogously to the working elements 86, 88 shown in FIG. 7.

The first working element 222 comprises a projection 226 and the second working element 224 comprises a projection 228, where the projections 226, 228 oppose one another in axial direction of the working elements. With this configuration of the instrument 22, an incision into the tissue or a vessel can also be made by rotating the instrument 220 about its axis or by moving the instrument 220 transversely to the axial direction.

An incision can be made by pushing the instrument 160 of FIG. 12 or the instrument 200 of FIG. 13 in axial direction, for example to cut through a vessel extending transversely to the axial direction of the working elements 162, 164 or 202, 204 or by moving the instruments in a direction transversely to the axial direction when the vessel extends parallel to the working elements.

As the above embodiments show, it is possible within the scope of the present invention to create corresponding cutting lines for electric cutting of tissue and vessels by a corresponding selection of the number and position of projections.

The form of the projections shown in the embodiments, which can be considered as being nipple-like, and the number of projections is to be understood to be exemplary. Any other form and number of projections can be provided when these are suited for causing a concentration of the current density of the high frequency current at their free ends to be able to perform electric cutting.

The free ends of the projections can also be rounded instead of being sharp-pointed, or projections can be provided with blade like elongated edges.

What is claimed is:

1. A bipolar medical instrument for cutting tissue comprising:
   a shaft having a distal end and a proximal end;
   a first working element disposed at said distal end of said shaft, said first working element being configured as an electrode connectable to high frequency current;
   at least one second working element disposed at said distal end of said shaft and adjacent to said first working element, said at least one second working element forming
   a counter electrode with respect to said first working element;
      wherein at least one of said first working element and said second working element comprises at least one projection, which is directed toward the other of said first and second working elements, and a free end of said at least one projection is configured such that a concentration of the current density occurs at said free end; and
      wherein said first working element and said second working element are each formed as jaws and are arranged side by side at a spacing from one another, such that said first working element and said second working element each comprise two jaw parts which are moveable with respect to one another, between which tissue can be grasped and coagulated.

2. The instrument of claim 1, wherein both said first working element and said second working element each comprise at least one projection.

3. The instrument of claim 2, wherein said at least one projection of said first working element opposes said at least one projection of said second working element.

4. The instrument of claim 1, wherein the at least one projection is directed to be inclined with respect to an axial direction of said working elements.

5. The instrument of claim 1, wherein said first working element extends beyond said second working element in axial direction of said working elements and wherein said at least one projection is directed in axial direction of said working elements.

6. The instrument of claim 1, wherein said free end of said at least one projection is configured as a point.

7. The instrument of claim 1, wherein said free end of said at least one projection is rounded.

8. The instrument of claim 1, wherein both said d first working element and said second working element each comprise at least one projection and said free end of said at least one projection of said first working element and said free end of said opposite projection of said second working element have a minimal spacing from one another.

9. The instrument of claim 1, wherein said free end of said at least one projection is configured as an elongated edge.

10. The instrument of claim 9, wherein said at least one projection runs in wedge-like manner at an inclination with respect to an axial direction of said working elements.

11. The instrument of claim 10, wherein both said first working element and said second working element have at least one projection formed as an elongated edge, and wherein each of said edges are formed to run at an inclination with respect to said axial direction of said working elements and wherein said opposing edges run counter directionally to one another.

12. The instrument of claim 1, wherein said first working element and said second working element are arranged to be immovable at a distal end of one or two rod-shaped elements.

13. The instrument of claim 12, wherein said rod-shaped element or said rod-shaped elements are configured to be electric conductors.

14. The instrument of claim 1, wherein said at least one projection is arranged on said first jaw part of one of said working elements and said at least one second projection is arranged on said second jaw part of said same working element.

15. The instrument of claim 1, wherein said first working element and said second working element are each formed as jaws, wherein said first working element and said second working element are arranged side by side at a spacing from one another, wherein said first working element and said second working element each comprise two jaw parts which are moveable with respect to one another, between which tissue can be grasped and coagulated and said at least one projection of one of said working elements is arranged on said first jaw part of this working element and said at least one projection of said second working element is arranged on that jaw part of said other working element, which lies diametrically opposite to said first jaw part of said first working element.

16. The instrument of claim 15, wherein said at least two projections are arranged at a same position in axial direction of said working elements.

17. The instrument of claim 1, wherein said first working element and said of second working element are exchangeable.

18. A bipolar medical instrument for cutting tissue comprising:

a shaft having a distal end and a proximal end;

a first working element disposed at said distal end of said shaft, said first working element being configured as an electrode connectable to high frequency current;

at least one second working element disposed at said distal end of said shaft and adjacent to said first working element, said at least one second working element forming a counter electrode with respect to said first working element;

wherein at least one of said first working element and said second working element comprises at least one projection, which is directed toward the other of said first and second working elements, and a free end of said at least one projection is configured such that a concentration of the current density occurs at said free end; and wherein said first working element and said second working element are each formed as jaws and are arranged side by side at a spacing from one another, such that said first working element and said second working element each comprise two jaw parts which are moveable with respect to one another, between which tissue can be grasped and coagulated and said at least one projection of one of said working elements is arranged on said first jaw part and said at least one projection of said second working element is arranged on said second jaw part of said second working element, which lies diametrically opposite to said first jaw part of said first working element.

* * * * *